United States Patent
Yano et al.

(10) Patent No.: US 11,272,727 B2
(45) Date of Patent: Mar. 15, 2022

(54) METHOD FOR EXTRACTING SEA CUCUMBER SAPONIN-CONTAINING EXTRACT AND METHOD FOR MAINTAINING CONSTANT CONTENT THEREOF

(71) Applicants: ISF LLC, Sapporo (JP); Iwate Prefecture, Morioka (JP); Iwate Medical University, Iwate (JP); Sanshou Inc, Ofunato (JP); Ono Foods Co. Ltd, Kamaishi (JP)

(72) Inventors: Akira Yano, Kitakami (JP); Mitsuo Kishi, Shiwa-gun (JP); Takao Sawai, Sapporo (JP); Takao Sasaki, Ofunato (JP); Akio Ono, Kamaishi (JP)

(73) Assignees: ISF LLC, Hokkaido (JP); IWATE PREFECTURE, Iwate (JP); IWATE MEDICAL UNIVERSITY, Iwate (JP); SANSHOU INC, Iwate (JP); ONO FOODS CO. LTD, Iwate (JP)

(*) Notice: Subject to any disclaimer, the term of this patent is extended or adjusted under 35 U.S.C. 154(b) by 0 days.

(21) Appl. No.: 16/641,800

(22) PCT Filed: Aug. 18, 2018

(86) PCT No.: PCT/JP2018/030588
§ 371 (c)(1),
(2) Date: Feb. 25, 2020

(87) PCT Pub. No.: WO2019/044552
PCT Pub. Date: Mar. 7, 2019

(65) Prior Publication Data
US 2020/0390137 A1  Dec. 17, 2020

(30) Foreign Application Priority Data
Aug. 29, 2017  (JP) ............... JP2017-164884

(51) Int. Cl.
*A61K 35/616* (2015.01)
*A23L 33/10* (2016.01)

(52) U.S. Cl.
CPC ............ *A23L 33/10* (2016.08); *A61K 35/616* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 7,163,702 B1 * | 1/2007 | Avilov | ............ | A61P 37/04 424/572 |
| 2011/0003022 A1 * | 1/2011 | Baird | ............ | A01N 37/36 424/777 |
| 2017/0044201 A1 * | 2/2017 | Sobolik | ............ | C07H 15/256 |

FOREIGN PATENT DOCUMENTS

| CN | 106265413 A | 1/2017 |
|---|---|---|
| JP | 5-276971 A | 10/1993 |

(Continued)

OTHER PUBLICATIONS

Kregiel et al., Saponin-Based, Biological-Active Surfactants from Plants, accessed: May 5, 2021 <https://www.intechopen.com/books/application-and-characterization-of-surfactants/saponin-based-biological-active-surfactants-from-plants> (Year: 2017).*

Notification of Transmittal of Translation of the International Preliminary Report on Patentability (Forms PCT/IB/326) issued in counterpart International Application No. PCT/JP2018/030588 dated Mar. 12, 2020 with Forms PCT/IB/373, PCT/IB/338 and PCT/ISA/237, with English translation (18 pages).

(Continued)

*Primary Examiner* — Viren A Thakur
*Assistant Examiner* — Thanh H Nguyen
(74) *Attorney, Agent, or Firm* — Westerman, Hattori, Daniels & Adrian, LLP

(57) ABSTRACT

The method extracts an extract containing sea cucumber saponins. The extract is separated from sea cucumber meat exclusively by a specific heat treatment without conducting any chemical treatment with the use of an enzyme, ethanol, etc. The method includes: a step for heating sea cumbers (Continued)

from a starting temperature to a target heating temperature by a first temperature gradient; and a step for decreasing the temperature by a second temperature gradient that is gentler than the first temperature gradient to thereby extract the sea cucumber extract. The sea cucumber extract is stored as a sea cucumber extract material in the form of a liquid concentrate, etc. Then an appropriate amount of the sea cucumber extract material is added to, for example, another sea cucumber extract material having been separated and extracted from sea cucumbers with a lower saponin content.

2 Claims, 7 Drawing Sheets

(56) References Cited

FOREIGN PATENT DOCUMENTS

| | | |
|---|---|---|
| JP | 6-287111 A | 10/1994 |
| KR | 20090099226 A * | 9/2009 |

OTHER PUBLICATIONS

International Search Report dated Nov. 13, 2018, issued in counterpart CN Application No. PCT/JP2018/030588 (2 pages).
Written Opinion dated Nov. 13, 2018, issued in counterpart Application No. PCT/JP2018/030588, with English Translation. (12 pages).

* cited by examiner

|  | SAPONIN CONTENT PER 1 G WEIGHT |
|---|---|
| SEA CUCUMBER RAW MATERIAL | 0.122 ±0.062 mg/g |
| TREATED SEA CUCUMBER MEAT PORTION | 0.283 ±0.067 mg/g |
| EXTRACTED SEA CUCUMBER EXTRACT | 0.062 ±0.001 mg/g |

Fig. 8

|  | SAPONIN CONTENT PER 1 G WEIGHT |
|---|---|
| SEA CUCUMBER RAW MATERIAL | 0.156 ±0.078 mg/g |
| TREATED SEA CUCUMBER MEAT PORTION | 0.440 ±0.072 mg/g |
| EXTRACTED SEA CUCUMBER EXTRACT | 0.090 ±0.002 mg/g |

METHOD FOR EXTRACTING SEA CUCUMBER SAPONIN-CONTAINING EXTRACT AND METHOD FOR MAINTAINING CONSTANT CONTENT THEREOF

TECHNICAL FIELD

The present invention relates to a technique for extracting a constant amount of saponins from echinoderms such as sea cucumbers according to parts of the animals.

BACKGROUND ART

Various useful components that are effective for improving disease and the like are present in plants and animals, including glycosides (saponins) for example, and saponins of animal origin include triterpenoid glycosides contained in sea cucumbers (hereunder called "sea cucumber saponins"), such as frondoside A and saponins in the holotoxin family, including holotoxin A, holotoxin B, holotoxin A1 and holotoxin B1.

Of the sea cucumber saponins, the holotoxin family in particular is known to have disinfectant activity against fungi such as yeasts and *Candida*, while frondoside A is known to have anti-cancer activity that suppresses the proliferation of cancer cells.

In the past, the functions of sea cucumber saponins have been exploited in commercial products that include sea cucumber soaps using the surfactant effects of the saponins and athlete's foot medicines using the disinfectant effects against fungi, but no foods exploiting the functions of saponins have yet been developed.

One reason for this is that because the saponin contents of sea cucumber vary greatly by individual and production region, it has not been possible to obtain a stable supply of raw materials containing a constant percentage of sea cucumber saponins.

Consequently, to develop functional foods that exploit the functions of the saponins, there is demand for methods whereby sea cucumber-containing extracts containing large quantities of such useful components can be collected even if the raw materials are sea cucumbers that differ widely by individual and production region, and whereby the sea cucumber saponin content can be adjusted to obtain a constant content.

When using useful components in plants and animals, the conventional practice has been to perform hot water extraction (infusion) by boiling the plant or animal in hot water, and then either ingest this as is, or concentrate it by heating the aqueous solution.

In the case of sea cucumbers, one practice has been to first boil them in hot water, followed by heated drying, or else to eat the raw sea cucumbers as sashimi.

However, the problem with such a hot water extract is that it contains ingredients other than medicinal ingredients which may contribute unpleasant smells, bitterness or astringency, making it unsuitable for ingestion.

Moreover, when using techniques of concentration by heating an aqueous solution of a broth of boiled sea cucumber or the like, the problem is that the extraction rate of the useful ingredient (sea cucumber saponins) is low, so that for example no more than about 2 to 3 grams of saponins can be collected from 500 liters of aqueous solution.

Techniques are also known for chopping the sea cucumber and adding a solvent such as ethanol to extract the saponins, or placing the sea cucumber in hot water to elute the saponins, and then adding the eluate to a preparative chromatography tube with an internal diameter of about 10 to 50 mm, such as a C18 column (ODS column), and performing separation and purification with a HPLC (high performance liquid chromatography) device or the like. However, these techniques are not practical considering that the saponin purification costs are high, and the resulting saponins are considered a reagent or pharmaceutical preparation rather than a foodstuff, and must be approved as food additives before being re-added to foodstuffs.

Therefore, an invention has been proposed for extraction using enzymes, as shown for example in PTL 1 (Method for concentrating and purifying useful component in animal and vegetable).

CITATION LIST

Patent Literature

[PTL 1] Japanese Patent Application Publication No. H05-276971

SUMMARY OF INVENTION

Technical Problem

PTL 1 describes a method for concentrating and separating a glycoside component in an animal or plant by adding a glucose group donor and a glycosyltransferase to an aqueous solution containing glycosides including holotoxin A and holotoxin B to thereby react the glycosides with the glucose group donor and produce water-insoluble glycoside sugar chain adducts including glycosides with 10 to 40 glucose groups added thereto, and then separating and collecting only the glycoside sugar chain adducts.

However, if the process includes a step of eluting the holotoxins and other saponins contained in sea cucumber into an aqueous solution, they become dispersed in the aqueous solution.

A step of concentrating by a predetermined method is then required, and although the yield is greater in comparison with methods of concentrating by heating an aqueous solution of the broth, it remains around 50%, and the problem of low yield remains considering that a yield of at least about 90% is ideal.

Furthermore, because the method of PTL 1 uses an enzyme reaction, a few hours to about 20 hours are required for extraction, and there are also problems of production costs due to the costs of enzymes and the like.

Since the sugar chain structures of the saponins are important for the disinfectant effect against fungi, moreover, the intrinsic functions of the sea cucumber saponins cannot be expected in the method of PTL 1, in which the sugar chains are collected after being modified with an enzyme.

Moreover, when saponins such as holotoxins are used as active components of functional foods and pharmaceuticals, the component percentage needs to be kept constant, but since the saponin content differs greatly depending on the individual sea cucumber, the production region and the harvest season, it is difficult to manufacture a product with a constant saponin content.

In order to avoid such problems, it is an object of the present invention to extract an extract containing saponins such as holotoxins as useful components directly from sea cucumber bodies, without first boiling the sea cucumbers and eluting the active components in an aqueous solution, without using ethanol, enzymes or the like, and with very little alteration to the composition of the sea cucumbers.

Another object is to adjust the component percentages of the active components, which differ according to the living environment of the sea cucumber including the region, to a constant component percentage (hereunder called "maintaining constant content").

Incidentally, when sea cucumber bodies have been crushed and pulverized in an effort to extract saponins such as holotoxins as active components directly from the sea cucumber bodies, the active components have not been effectively pulverized due to the presence of excess components. Regarding efforts extract active components by heating the sea cucumber bodies directly, it has not been possible to extract the saponins from the sea cucumbers themselves because the body tissues dissolve at about 20° C. when the sea cucumbers are removed from the ocean and left in the air, and the sea cucumber saponins and collagen partially decompose to produce an undifferentiated gelatinous mass.

Therefore, in the past the most common method of processing sea cucumbers has been to remove the viscera, wash the sea cucumber meat, immediately boil it in a large quantity of hot water to prevent quality deterioration, and then dry it or process it with salt.

In the present technique, by first washing the sea cucumber meat and then subjected it to heating and cooling with predetermined temperature gradients to thereby transform and stably fix the collagen before the sea cucumber could dissolve, we succeeded in separating a sea cucumber meat portion containing many collagen fibers and a sea cucumber extract containing many saponins and amino acids directly from the sea cucumber body.

We also succeeded in obtaining a constant content by suitably adjusting the separation ratios of the sea cucumber meat portion and the sea cucumber extract.

It was thus possible to obtain a sea cucumber extract material containing many sea cucumber saponins, and by storing the extracted sea cucumber extract containing many sea cucumber saponins in the form of a concentrated liquid or dried powder and using it in combination with a sea cucumber raw material with a low sea cucumber saponin content, it was possible to achieve a constant content of saponins.

For example, using sea cucumbers from a region where the saponin content is high as a raw material, a sea cucumber meat portion and sea cucumber extract can be separated and extracted from the sea cucumber material, and the sea cucumber meat portion can be dried and pulverized to manufacture a sea cucumber material, or the sea cucumber extract can be concentrated or dried and then powdered and stored as a sea cucumber extract material (liquid concentrate or dried powder), and a suitable amount of the sea cucumber extract material with a high saponin content can then be added to a dried powder made from sea cucumbers from a region where the saponin content is low to thereby adjust the saponin content to a constant level.

Solution to Problem

Corresponding to Descriptions of Claims

To achieve the above objects, a first invention is preferably a method for extracting a sea cucumber extract from sea cucumbers by heat treatment, the method including: a step of rapidly heating sea cucumbers to an initial heating temperature (40° C.); a temperature increase step in which the temperature of the sea cucumbers is increased from the initial heating temperature to at least not less than a target heating temperature with a first temperature gradient; a step of determining whether the temperature of the sea cucumbers has been increased to at least not less than the target heating temperature; a temperature decrease step in which once the target temperature has been reached, the temperature of the sea cucumbers is decreased with a second temperature gradient that is gentler than the first temperature gradient; and a step of determining whether the temperature of the sea cucumbers has been decreased to at least not more than a decrease target temperature, whereby the sea cucumber extract containing the sea cucumber saponin is separated from a sea cucumber meat portion and extracted from the sea cucumbers simply by heat treatment without any chemical treatment using enzymes, ethanol or the like.

A second invention is preferably the method for extracting a sea cucumber extract, wherein the first temperature gradient in the temperature increase step of increasing the temperature of the sea cucumbers to not less than the target heating temperature is in the range of 0.7° C./minute to 1.5° C./minute, and the second temperature gradient in the temperature decrease step of decreasing the temperature of the sea cucumbers to not more than the decrease target temperature is 1.0° C./2 minutes to 1.0° C./5 minutes.

A third invention is preferably a method for manufacturing a foodstuff or formulation containing a sea cucumber saponin at a percentage of a predetermined reference value by combining a sea cucumber material and/or sea cucumber extract material containing the sea cucumber saponin at a percentage above the predetermined reference value with a sea cucumber material and/or sea cucumber extract material containing the sea cucumber saponin at a percentage below the predetermined reference value, the method including: a first manufacturing step of manufacturing the sea cucumber material and/or sea cucumber extract material containing the sea cucumber saponin at a percentage above the predetermined reference value by drying and then fine pulverizing or concentrating a sea cucumber meat portion or sea cucumber extract that has been separated and extracted by the above method according to the first invention for extracting a sea cucumber extract from a sea cucumber raw material from a production region where sea cucumbers have a high sea cucumber saponin content; a second manufacturing step of manufacturing a sea cucumber material and/or sea cucumber extract material containing the sea cucumber saponin at a percentage below the predetermined reference value by drying and then fine pulverizing or concentrating a sea cucumber meat portion or sea cucumber extract that has been separated and extracted by the above method for extracting a sea cucumber extract from a sea cucumber raw material from a production region where sea cucumbers have a low sea cucumber saponin content; and a third manufacturing step of mixing the sea cucumber material or sea cucumber extract material obtained in the first manufacturing step with the sea cucumber material or sea cucumber extract material obtained in the second manufacturing step, whereby a sea cucumber material and/or sea cucumber extract material containing the sea cucumber saponin at a percentage of the predetermined reference value, or a foodstuff or formulation containing the sea cucumber material and/or sea cucumber extract material.

Furthermore, a sea cucumber material or sea cucumber extract material containing a sea cucumber saponin is available, which is obtained by drying and then fine pulverizing or concentrating a sea cucumber meat portion or sea cucumber extract separated from sea cucumbers by the method for extracting a sea cucumber extract according to the first or second invention.

Furthermore, a sea cucumber material and/or sea cucumber extract material containing a sea cucumber saponin at a percentage of a predetermined reference value, or a foodstuff or formulation containing the sea cucumber material or sea cucumber extract material is available, which is manufactured by the manufacturing method of the third invention.

A fourth invention is preferably a system for extracting a sea cucumber extract by heat treatment from sea cucumbers, the system including: measures for rapidly heating sea cucumbers to an initial heating temperature; a temperature increase gradient adjustment measures whereby the temperature of the sea cucumbers is increased from the initial heating temperature to at least not less than a target heating temperature with a first temperature gradient; and a temperature decrease gradient adjustment measures whereby once the temperature of the sea cucumbers has reached at least the target temperature, the temperature of the sea cucumbers is decreased with a second temperature gradient that is gentler than the first temperature gradient, wherein by decreasing the temperature of the sea cucumbers to at least not more than a decrease target temperature, a sea cucumber extract containing a sea cucumber saponin is separated from a sea cucumber meat portion and extracted from the sea cucumbers simply by heat treatment without any chemical treatment using enzymes, ethanol or the like.

The fifth invention is preferably the system for extracting a sea cucumber extract according to the fourth invention, wherein the first temperature gradient in the temperature increase gradient adjustment measures of increasing the temperature of the sea cucumbers to not less than the target heating temperature is in the range of 0/7° C./minute to 1.5° C./minute, and the second temperature gradient in the temperature decrease gradient adjustment measures of decreasing the temperature of the sea cucumbers to not more than the decrease target temperature is 1.0° C./2 minutes to 1.0° C./5 minutes.

The sixth invention is preferably a system for manufacturing a foodstuff or formulation containing sea cucumber saponins at a percentage of a predetermined reference value by combining a sea cucumber material and/or sea cucumber extract material containing the sea cucumber saponin at a percentage above the predetermined reference value with a sea cucumber material and/or sea cucumber extract material containing the sea cucumber saponin at a percentage below the predetermined reference value, the system including: a first manufacturing measures for manufacturing the sea cucumber material and/or sea cucumber extract material containing the sea cucumber saponin at a percentage above the predetermined reference value by drying and then fine pulverizing or concentrating a sea cucumber meat portion or sea cucumber extract that has been separated and extracted by the above system for extracting a sea cucumber extract by the system according to the invention 4 from a sea cucumber raw material from a production region where sea cucumbers have a high sea cucumber saponin content; a second manufacturing measures for manufacturing the sea cucumber material and/or sea cucumber extract material containing the sea cucumber saponin at a percentage below the predetermined reference value by drying and then fine pulverizing or concentrating a sea cucumber meat portion or sea cucumber extract that has been separated and extracted by the above system for extracting a sea cucumber extract by the system according to the invention 4 from a sea cucumber raw material from a production region where sea cucumbers have a low sea cucumber saponin content; and a third manufacturing measures for mixing the sea cucumber material or sea cucumber extract material obtained by the first manufacturing measures with the sea cucumber material or sea cucumber extract material obtained by the second manufacturing measures, whereby a sea cucumber material and/or sea cucumber extract material containing the sea cucumber saponin at a percentage of the predetermined reference value, or a foodstuff or formulation containing the sea cucumber material and/or sea cucumber extract material is manufactured.

Advantageous Effects of Invention

With the method of the invention for extracting and maintaining a constant content of sea cucumber saponins such as holotoxins, a sea cucumber extract can be separated and extracted from a sea cucumber meat portion, and a sea cucumber extract with a high saponin content can be extracted.

Since the sea cucumber extract has a composition similar to that of the original sea cucumber raw material except that it is a so-called sea cucumber broth that does not contain the fibers and the like constituting the animal tissue, it can also be used as a food material.

Furthermore, by storing a sea cucumber meat portion or sea cucumber extract that has been separated and extracted from sea cucumbers with a high saponin content as a sea cucumber material (dried powder, etc.) or sea cumber extract material (liquid concentrate, dried powder, etc.), and then adding a suitable amount thereof to a sea cucumber material or sea cucumber extract material that has been extracted from sea cucumbers with a low saponin content, it is possible to provide a sea cucumber material or sea cucumber extract material with a saponin content maintained at a constant level, as well as a functional food using these.

Using this technology, it is possible to develop foodstuffs with fungicidal activity and excellent mold resistance, and to manufacture functional foods and the like for preventing oral *Candida* infection. Since many elderly people and people requiring care suffer from *Candida* infections, a foodstuff or the like that suppresses *Candida* is expected to be important.

It can also be used as a naturally mold resistant food material. It is also expected to have various other applications as a novel material that can provide the various effects of sea cucumber saponins.

BRIEF DESCRIPTION OF DRAWINGS

FIG. 8 is another example showing contained concentrations of saponins in a sea cucumber meat portion and sea cucumber extract prepared by the extraction steps of the invention from *Apostichopus japonicus* from a specific location.

EXPLANATION OF TERMS

"Saponins" here mean glycosides, and saponins of animal origin include triterpenoid glycosides contained in sea cucumbers, such as a saponin called frondoside A and saponins in the holotoxin family, including holotoxin A, holotoxin B, holotoxin A1 and holotoxin B1. Of the sea cucumber saponins, the holotoxin family in particular is known to have disinfectant activity against fungi such as yeasts and *Candida*, while frondoside A is known to have anti-cancer activity that suppresses the proliferation of cancer cells.

"Sea cucumber saponins" is a general term for saponins such as frondoside A and the holotoxin A, holotoxin B, holotoxin A1 and holotoxin B1 and the like described above.

"Sea cucumber meat portion" is the meat part that remains after extraction of sea cucumber extract from sea cucumbers, and is also called sea cucumber meal. It contains sea cucumber saponins, and is dried as is and used as dried sea cucumber, or used as a powder. Because of their commercial value, spiky *Apostichopus japonicus* and the like are often left in their original shape when making dried sea cucumber.

"Sea cucumber extract" is the sea cucumber drip (heating-cooling exudate) exuded by sea cucumbers when they are heated and cooled with predetermined temperature gradients.

A "sea cucumber material" is a material produced by drying and pulverizing the sea cucumber meat portion.

A "sea cucumber extract material" is a material produced by concentrating or drying and pulverizing the extracted sea cucumber extract.

"Sea cucumber powder" is a powder formed of a mixed powder of sea cucumber material and sea cucumber extract material.

Various methods such as natural drying, hot air drying, fluidized bed drying, low-temperature drying, freeze drying and pressure drying can be used as the drying method.

DESCRIPTION OF EMBODIMENTS

Examples of the system of the invention for extracting a sea cucumber extract containing sea cucumber saponins are explained below.

Sea cucumbers here are used only as an example, and the invention can also be applied to sea urchins and other echinoderms in the same phylum as sea cucumbers.

Figure 1:
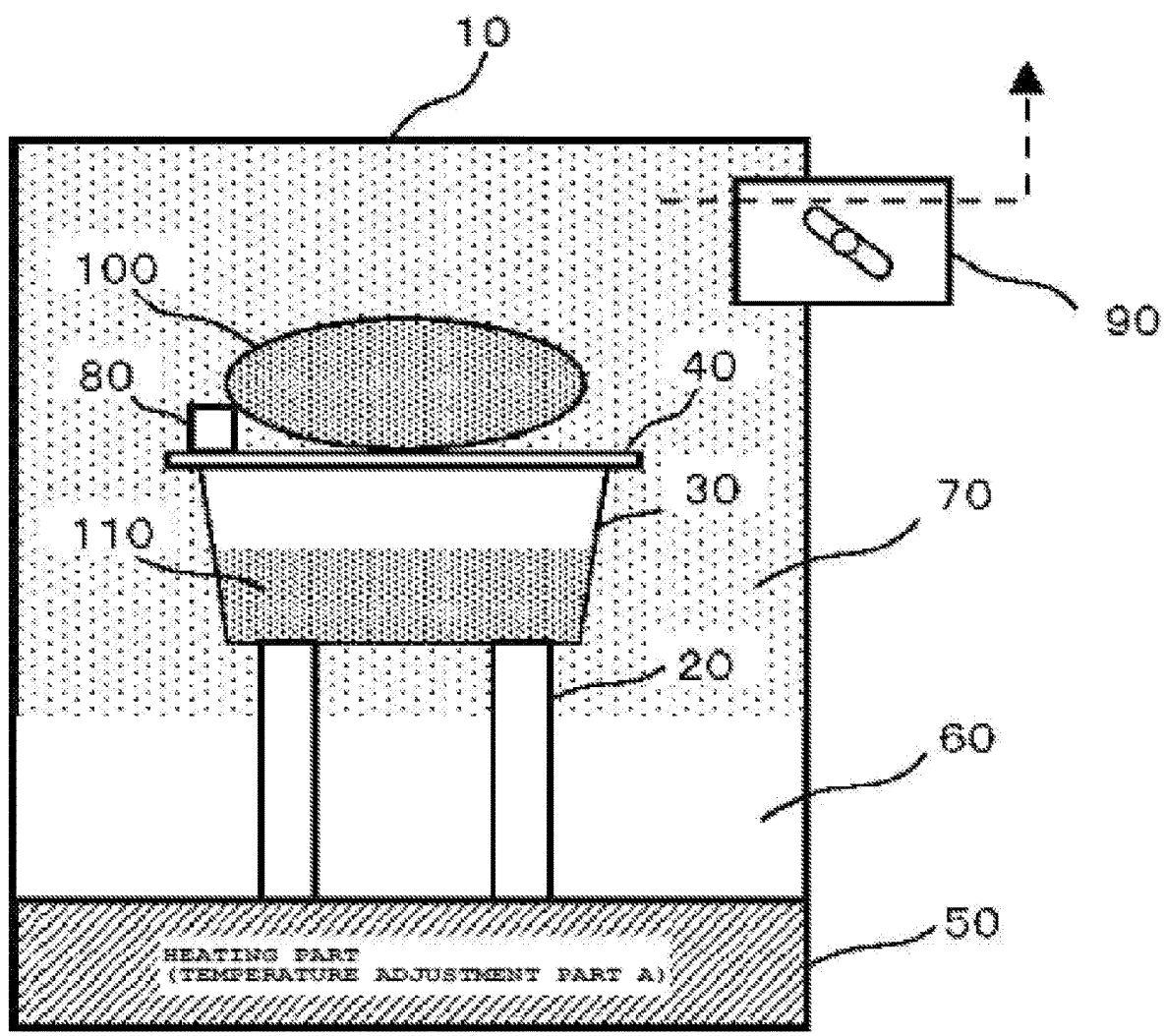
FIG. 1 shows one example of a sea cucumber saponin extraction system of the invention.

1. Outline of System of Invention for Extracting Sea Cucumber Extract Containing Sea Cucumber Saponins Methods for extracting sea cucumber extract directly from sea cucumbers are explained first with reference to the diagram of FIG. 1 showing the configuration of a sea cucumber extract extraction system 10 of the invention.

The sea cucumber extract extraction system 10 is provided with a net or other sea cucumber support part 40 for holding a sea cucumber 100, an extract extraction part 30 for accumulating the sea cucumber extract 110 extracted from the sea cucumber 100, and legs 20 for supporting these members.

The sea cucumber extract extraction system 10 is also provided with a heating part (temperature adjustment part A) 50, which is an electric heater, gas burner or the like for heating water to obtain hot water 60 and generate steam 70.

It is also provided with a temperature measurement part 80 for measuring the temperature of the sea cucumber, and a release valve adjustment part (temperature adjustment part B) 90 for adjusting the temperature increase and decrease by opening and closing a valve or the like. Moreover, although this is not shown, the system may also be configured so that steam can be forcibly discharged with an electric fan or the like to perform rapid adjustments such as lowering the temperature.

The heating part (temperature adjustment part A) 50 and release valve adjustment part (temperature adjustment part B) 90 can also be configured so that the temperature is raised or lowered by a predetermined temperature gradient through feedback control from a computer or control mechanism based on information from the temperature measurement part 80, or to allow an operator to raise or lower the temperature with a predetermined temperature gradient after observing the data from the temperature measurement part 80.

Although these are not shown, various methods are possible such as adjusting the temperature of the steam with a separate mechanism and then blowing the steam directly onto the sea cucumber, and it is sufficient that the system be configured so that the temperature of the sea cucumber can be raised and lowered by a predetermined temperature gradient.

Using such a configuration, the gradients of the temperature increase (heating) and temperature decrease (cooling) of the steam 70 are adjusted to heat and cool the sea cucumber predetermined temperature gradients and extract a sea cucumber extract from the sea cucumber.

More specifically, water is heated by the heating part (temperature adjustment part A) 50 to generate steam 70 from hot water 60, and using the high specific heat of water, the appreciable amount of heat of the steam 70 is used to heat the sea cucumber 100, which is heated to a predetermined temperature within a specific amount of time to thereby heat denature the collagen component contained in the body walls of the sea cucumber.

The temperature of the sea cucumber 100 is then lowered to a predetermined temperature within a specific amount of time by means of the release valve adjustment part (temperature adjustment part B), to thereby fix the heat denatured collagen component in a stable state and prevent the collagen component and sea cucumber extract from mixing as the denatured and fixed collagen component (sea cucumber meat portion 100) is separated from a sea cucumber extract 110 containing many sea cucumber saponins.

The sea cucumber extract separated and extracted from the sea cucumber meat portion flows out of the sea cucumber meat proportion and passes through the sea cucumber support part 40 (which is composed of a net or the like) to accumulate in the extract extraction part 30.

It has been found that while the extracted sea cucumber extract contains many sea cucumber saponins, the sea cucumber meat portion also contains many sea cucumber saponins, and can be used as a sea cucumber material as explained below.

The gradient of the temperature increase per unit time is achieved by using a combination of the heating part (temperature adjustment part A) and the release valve adjustment part (temperature adjustment part B), while the gradient of temperature decrease is achieved mainly using the release valve adjustment part (temperature adjustment part B), although other measures are possible.

Furthermore, the extraction system of FIG. 1 is only one example: any mechanism capable of raising the temperature of sea cucumbers with a predetermined temperature gradient and lowering the temperature (cooling) with a predetermined temperature gradient is sufficient, and many examples are possible.

Figure 2:
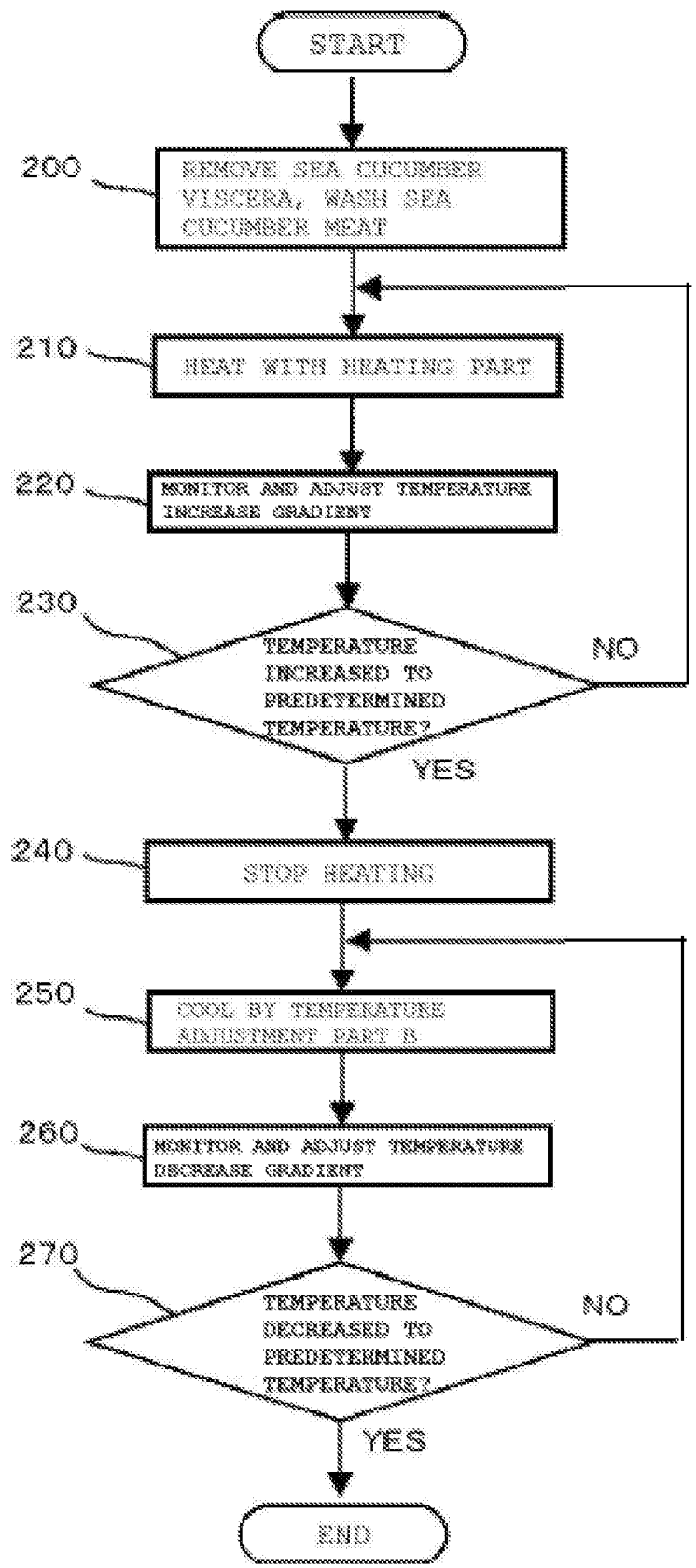
FIG. 2 shows one example of the overall flow of sea cucumber saponin extraction steps in the invention.

2. Overall Flow of System of Invention For Extracting Sea Cucumber Extract Containing Sea Cucumber Saponins Next, the overall flow of the system of the invention for extracting a sea cucumber extract is explained with reference to FIG. 2.

The sea cucumber viscera are first removed, and the sea cucumber meat is washed (step 200). Heating is then initiated by the heating part (temperature adjustment part A) 50 (step 210), and once the temperature of the steam 70 has been raised to a predetermined temperature (about 40° C.) the sea cucumber is placed therein, and the internal temperature of the sea cucumber is rapidly raised to the initial heating temperature of 40° C. (not shown).

Next, the internal temperature of the sea cucumber is measured as the temperature of the steam 70 is raised by means of the heating part 50 and the gradient of the increase in the internal temperature of the sea cucumber (step 220) is adjusted while monitoring whether the temperature increase per unit time or in other words the predetermined temperature increase gradient is obtained.

The temperature of the sea cucumber is preferably measured by measuring the internal temperature of the sea cucumber, but it is possible instead to measure the surface temperature of the sea cucumber or the temperature of the atmosphere near the sea cucumber in advance, record the correlation between this and the internal temperature of the sea cucumber, and then substitute measurements of the surface temperature of the sea cucumber or the temperature of the atmosphere near the sea cucumber.

The applicants here ascertained as a result of thousands of trials and errors that when the initial value of the temperature of the steam applied to a sea cucumber is about 40° C., the optimum value of the temperature gradient during the subsequent temperature increase (first temperature gradient) is 1.0° C. per minute.

Looking at the minimum temperature to which the temperature needs to be raised (heating target temperature), we also ascertained that raising the temperature to at least about 65° C. is optimal.

Figure 3:
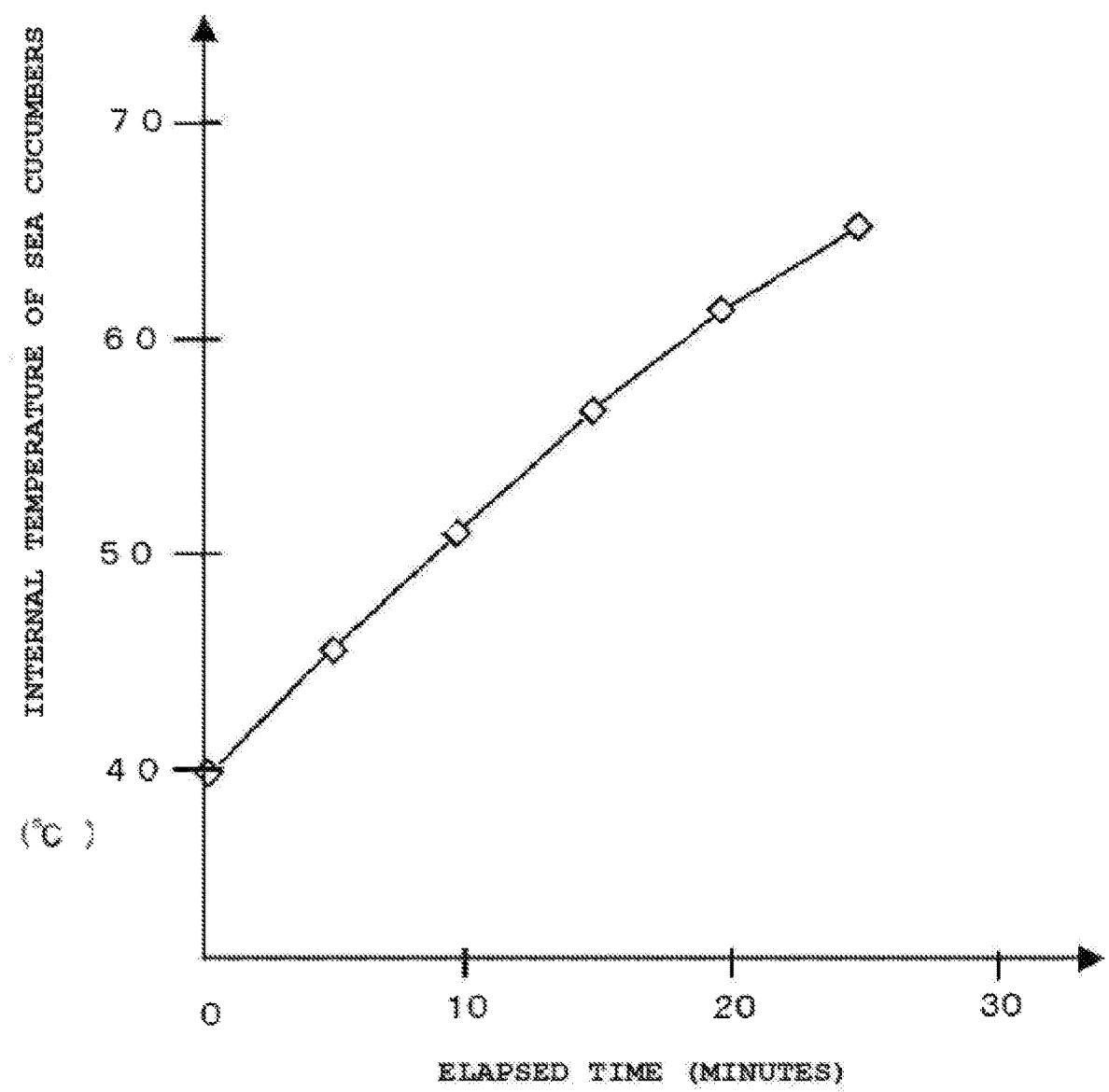
FIG. 3 shows a temperature gradient during temperature increase in a sea cucumber saponin extraction step of the invention.

The temperature gradient of the internal temperature of the sea cucumber during this temperature increase is shown in FIG. 3, which shows that the temperature increase gradient is generally about 1.0° C./minute.

This initial value and temperature increase gradient are not limited to the above optimal values. Large improvements in saponin yield in comparison with prior art are still possible within a certain range, and it has been shown that a sea cucumber extract containing sufficient saponins can be extracted if the initial value of the temperature of the steam 70 when adding the sea cucumber is in the range of 35° C. to 45° C.

Similarly, it has been shown that satisfactory sea cucumber extract extraction is possible if the temperature gradient during temperature increase is in the range of roughly 0.7° C. to 1.5° C./minute.

The minimum temperature to which the temperature needs to be raised may also be below the optimal temperature of 65° C., and it has also been shown that satisfactory sea cucumber extract extraction is possible if the temperature is raised to at least about 60° C.

Next, the increase of the temperature to the predetermined temperature (about 65° C.) is monitored, and if the predetermined temperature is determined to have been reached (step 230), heating is stopped (step 240).

After a predetermined stabilization time, the valve is opened and closed by means of the release valve adjustment part (temperature adjustment part B) 90 to lower the temperature of the steam 70 (step 250), and valve opening and closing is adjusted while monitoring whether the temperature gradient of the internal temperature of the sea cucumber during temperature decrease (cooling) is the predetermined gradient (step 260).

The temperature decrease to a predetermined temperature that is the target value of the temperature decrease is verified (step 270), and separation and extraction treatment is complete when the temperature has fallen to the predetermined temperature (about 40° C.) or less.

The sea cucumber extract that has been separated and extracted from the sea cucumber meat portion by the above steps flows out of the sea cucumber, passes through the sea cucumber support part 40 composed of a net or the like, and accumulates in the extract extraction part 30.

It has been shown that the sea cucumber extract is separated and extracted from the sea cucumber meat portion and flows out of the sea cucumber meat portion during the temperature decrease flow from step 250 to step 260 in particular.

The applicants ascertained as a result of thousands of trials and errors that the optimum value of the temperature gradient during temperature decrease (second temperature gradient) is gentler than about 1.0° C./3 minutes (including 1.0° C./3 minutes, 1.0° C./4 minutes, 1.0° C./5 minutes and the like).

Figure 4:
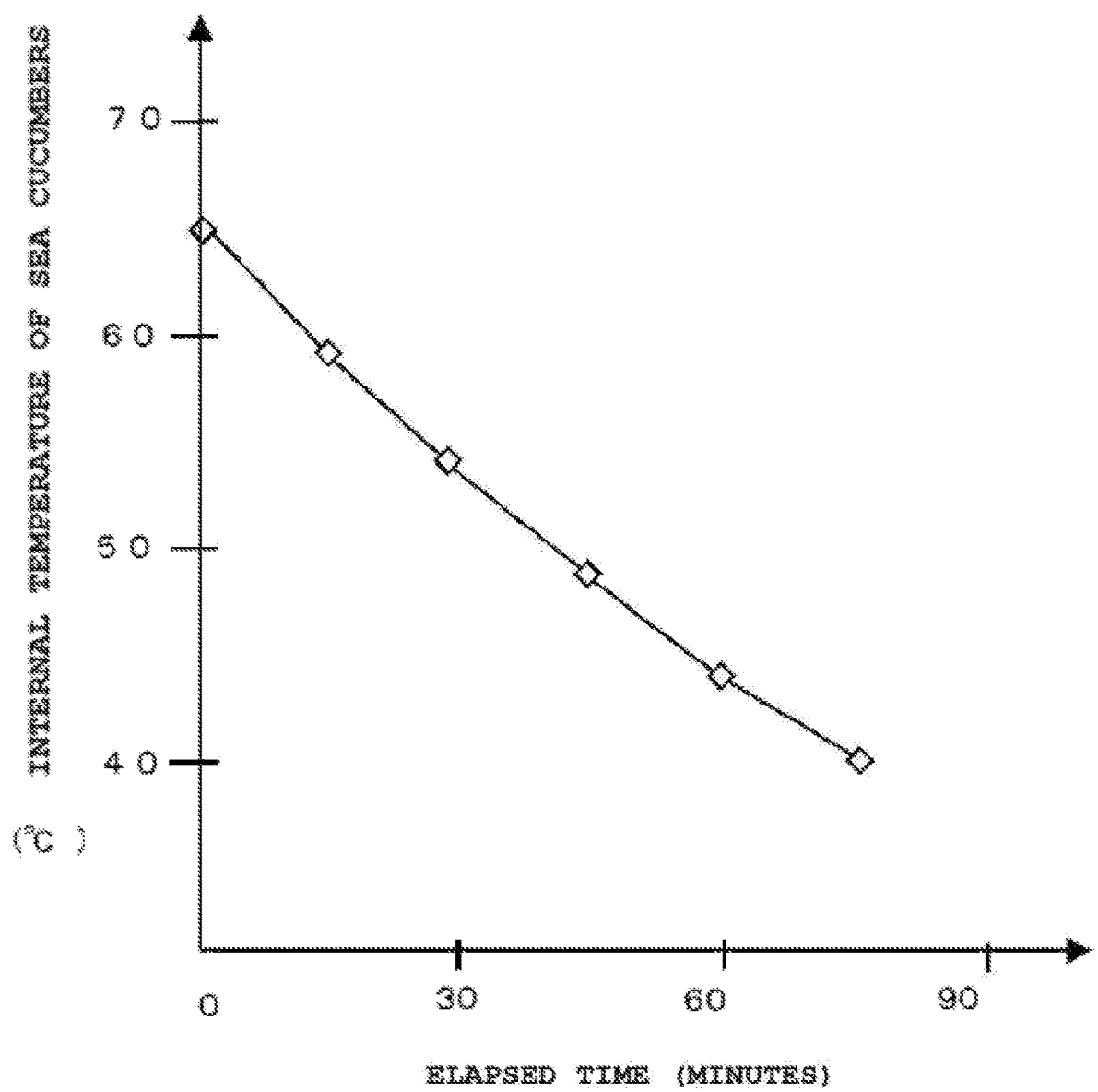
FIG. 4 shows a temperature gradient during temperature decrease in a sea cucumber saponin extraction step of the invention.

FIG. 4 shows the temperature gradient of the internal temperature of the sea cucumber during this temperature decrease.

The temperature gradient during temperature decrease here is optimally gentler than 1.0° C./3 minutes, but it has been shown that a sea cucumber extract that is sufficiently superior to prior art can be obtained with a gradient that is gentler than about 1.0° C./2 minutes.

Moreover, the decrease target temperature during temperature decrease (about 40° C.) is an optimal value, and it has been shown that a sufficient quantity of sea cucumber extract can be extracted if the temperature is somewhat higher or lower.

It has been shown that the optimum value of the temperature gradient during temperature decrease is determined in combination with the temperature gradient during temperature increase, with the optimum values being 1.0° C./minute for the temperature gradient during temperature increase and gentler than 1.0° C./3 minutes for the tempera- 3. Association Between Sea Cucumber Saponins and Collagen Depending on Application of Temperature Increase and Decrease Gradients, and Mechanism of Sea Cucumber Saponin Extraction Next we discuss the association between sea cucumber saponins and body tissue including collagen fibers and the like depending on how such temperature increase and decrease gradients are applied.

As discussed above, when sea cucumbers were removed from sea water and left in air at room temperature (20° C.), the body tissue dissolved, and the sea cucumber saponins and collagen unraveled to produce an undifferentiated gelatinous mass, making it impossible to extract sea saponins from the sea cucumber itself.

In general, body tissue containing collagen fiber and the like in marine organisms is known to dissolve at lower temperatures than body tissue containing collagen and the like in terrestrial organisms, and this is thought to be because they have evolved to produce collagen that is not denatured up to temperatures slightly higher than the environment in which the organism lives.

Sea cucumbers are marine organisms, and their body tissue containing collagen fiber is known to dissolves at low temperatures of about 20° C. as discussed above.

The exact mechanism of dissolution has not been completely elucidated, but it is thought that in sea cucumbers, body tissues containing collagen fiber relax or harden in response to external temperatures, and when left at room temperatures, the mechanism that adjusts the hardness of the tissue breaks down.

Consequently, we achieved a method for extracting a sea cucumber extract containing sea cucumber saponins by applying a temperature of a predetermined initial value before the body tissue containing collagen fiber and the like dissolves, raising the temperature at a predetermined temperature gradient to denature the collagen, and then cooling the denatured collagen at a predetermined temperature gradient to stably fix the collagen and solidify the sea cucumber meat portion and prevent it from mixing with the sea cucumber saponins.

The mechanism whereby the sea cucumber meat portion is solidified and a sea cucumber extract containing sea cucumber saponins can be extracted by raising and lowering the temperature by predetermined temperature gradients is not completely understood, but is generally thought to be as follows.

The tissue making up sea cucumber body walls is called connective tissue, and is used instead of muscle for solidifying body walls and moving spines. Unlike human collagen, the collagen in the body walls forms unbranched collagen fibers.

Water constitutes most (90% or more) or the sea cucumber's body walls, with the remainder being composed of proteins such as collagen and active components such as saponins.

Collagen is known to constitute about 70% to 80% of the proteins making up the sea cucumber's body walls, with most (20% to 30%) of the remainder being unique proteins having a fibronectin-like structure. Fibronectin is an adhesion protein present in many animals, and plays an important role in maintaining cell morphology by binding with cells and fibrous proteins.

The body walls of sea cucumbers are composed of irregularly arranged fibrous muscle material, and this fibrous muscle material consists mainly of fibrous collagen (fibrous proteins) which form a three-dimensional mesh that envelops relatively large quantities of body fluids (saponins and the like).

Thus, it is thought that the proteins such as fibrous collagen and the like in sea cucumbers maintain a constant morphology (three-dimensional structure) due to the adhesion action of fibronectin, but fibronectin is also liable to heat denaturation, so when the sea cucumber is left at room temperature and its temperature rises above that of the growth environment, the adhesion action of the fibronectin is weakened so that the three-dimensional structure breaks down and a constant morphology cannot be maintained, or the fibrous collagen is heat denatured and the fibrous tangles are weakened, causing the saponins that were held in the mesh to become mixed in with the resulting undifferentiated gelatinous mass. In this state, there is also a risk that sea cucumber enzymes may promote decomposition of the saponins.

Therefore, it is thought that when heat is applied at a predetermined, relatively high initial temperature (about 40° C.) so that the sea cucumber body tissue including the collagen fibers and the like does not pass slowly (passes rapidly) through the dissolution temperature (about 20° C.), the temperature is increased with a relatively rapid predetermined temperature gradient (1.0° C./minute) to denature the constituent proteins of the body walls, and cooling is then performed at a somewhat slower temperature gradient (1.0° C./3 minutes) to stably solidify the denatured constituent proteins, the constituent proteins are consolidated as a sea cucumber meat portion and prevented from mixing with the sea cucumber saponins, and the sea cucumber saponins that were held in the mesh are released from the mesh and extracted.

If the temperature increase gradient is relaxed from the optimal 1.0° C./1 minute to 1.0° C./2 minutes (slow temperature increase), more of the body tissue including the collagen fibers and the like is dissolved, increasing the rate of mixing between the constituent proteins and the sea cucumber saponins, and reducing the sea cucumber saponin extraction level. Conversely, if the temperature increase gradient is sped up from the optimal 1.0° C./1 minute to 1.0° C./0.5 minutes the constituent protein denature too rapidly, and more of the sea cucumber saponins become trapped in the mesh, decreasing the extraction level of sea cucumber saponins.

If the temperature decrease gradient is sped up from the optimal 1.0° C./3 minutes to 1.0° C./2 minutes, 1.0° C./1 minute or the like (if cooling is too fast), the quantity of sea cucumber saponins released from the mesh is reduced, and the extraction level is lower.

It has also been shown that if the internal temperature of the sea cucumber is raised all at once to 65° C., it shrinks without hardening, indicating that the way in which the temperature increase and decrease gradients are applied is important.

4. Adjusting Extracted Amount of Saponins

It has been shown as a result of experiments that if the temperature gradient during temperature decrease is further relaxed from the optimal 1.0° C./3 minutes of FIG. 4 to 1.0° C./4 minutes or 1.0° C./5 minutes (not shown), more sea cucumber saponins are extracted, and fewer sea cucumber saponins remain in the sea cucumber meat portion.

This may be associated with the time taken for the modified constituent proteins to stabilize and solidify and the effect of the mesh pushing out the extract as it thermally contracts, and it is thought that a gradual cooling process gives the sea cucumber saponins more time to be released from the mesh.

Thus, with the system and method of the present invention not only can sea cucumber saponins contained in a sea cucumber extract be separated from the sea cucumber meat portion in a sea cucumber extract, but the rate of separation can also be adjusted.

5. Method for Maintaining Constant Content to Adjust Differences Between Individual Sea Cucumbers and Regional Differences Between Production Regions Next, a method for obtaining a constant content is explained whereby a stable a functional food or formulation containing a stable percentage of saponins, which could not be provided in the past due to large differences in sea cucumber saponin contents depending on the individual sea cucumbers, regional differences between production regions and seasonal differences, can be provided with a constant percentage by the method and system of the invention.

Figure 5:
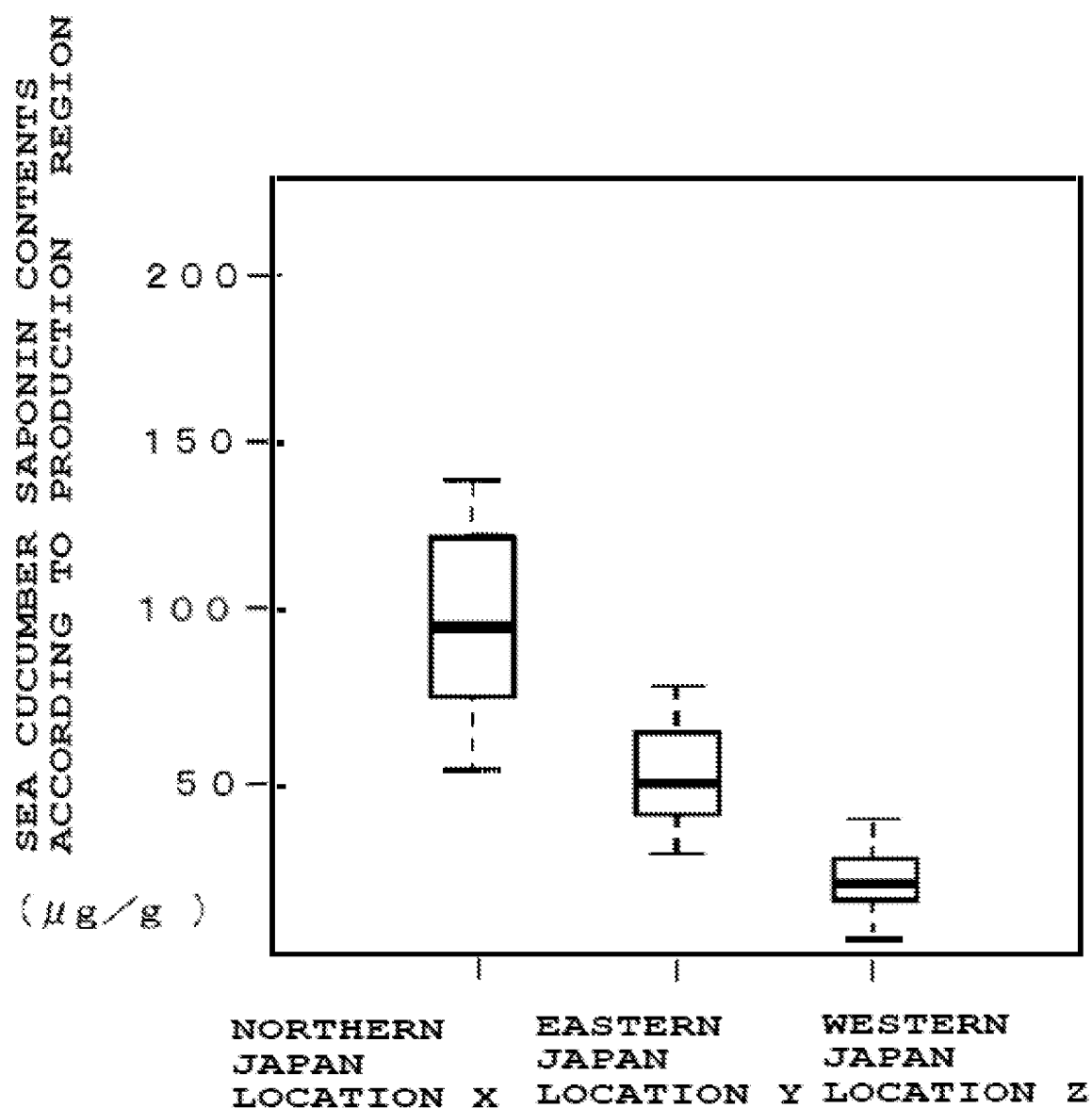
FIG. 5 shows the contained concentration of sea cucumber saponins in *Apostichopus japonicus* according to production region.

As shown in FIG. 5, the applicants' investigations over time have shown that concentrations of sea cucumber saponins exhibit large regional differences between production regions, and this difference may be five-fold or more. The range of the variation in concentration is shown by the marks "−" above and below, while the range within the predetermined standard deviation is shown by a box, and the representative value within the box is shown with a bold horizontal line.

Figures 6, 7:
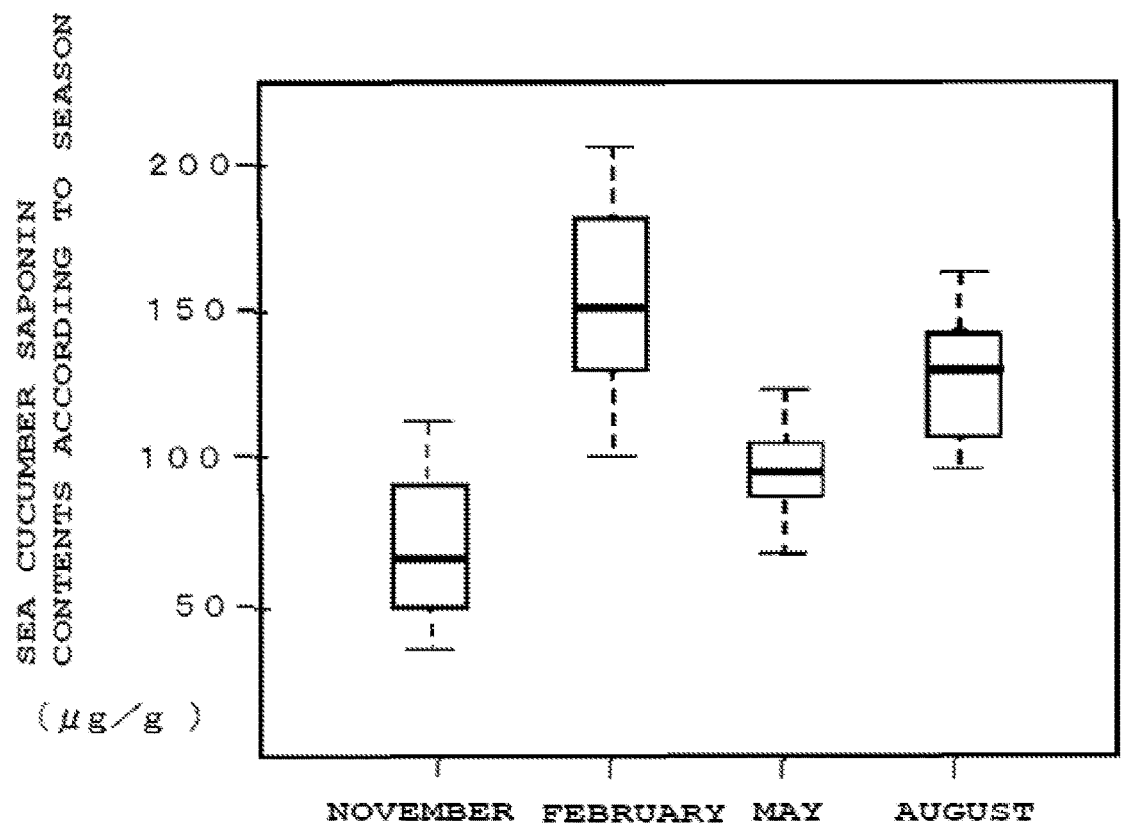
FIG. 6 shows changes in the contained concentration of sea cucumber saponins in *Apostichopus japonicus* according to season.
FIG. 7 shows contained concentrations of saponins in a sea cucumber meat portion and sea cucumber extract prepared by the extraction steps of the invention from *Apostichopus japonicus* from a specific location.

As shown in FIG. 6, moreover, concentrations of sea cucumber saponins also differ greatly according to season, and there may be a 2-fold to 5-fold difference within the same production region.

With the system and method of the present invention, since sea cucumbers can be separated into a sea cucumber meat portion and a sea cucumber extract while extracting the sea cucumber saponins, sea cucumbers can be collected from a region or season when the sea cucumber saponin content is high, and used to make a liquid concentrate or dried powder of a sea cucumber material or sea cucumber extract material containing many saponins, so that even if this is combined with a sea cucumber material or sea cucumber extract material extracted from a sea cucumber raw material with fewer sea cucumber saponins, the amount of saponins can be kept constant.

For example, sea cucumbers from a region where the saponin content is high can first be used as a raw material to manufacture a sea cucumber extract material (liquid concentrate or dried powder), and a suitable amount of the sea cucumber extract material (liquid concentrate or dried powder) with the high saponin content can be added to a dried powder made using sea cucumbers from a region where the saponin content is low as a raw material to thereby adjust the saponin content to a constant level.

More specifically, for example sea cucumbers from location X in northern Japan are collected at a specific season when the sea cucumber saponin content is high, and separated into a sea cucumber meat portion and a sea cucumber extract to thereby extract a sea cucumber extract containing many sea cucumber saponins, and this sea cucumber extract is then stored as a sea cucumber extract material (liquid concentrate or dried powder).

Sea cucumbers from location Z in western Japan where the sea cucumber saponin content is ordinarily low are then collected at a specific season when the sea cucumber saponin content is high, and separated into a sea cucumber meat portion and a sea cucumber extract to thereby extract a sea cucumber extract containing few sea cucumber saponins, and a suitable amount of the previously stored sea cucumber material (liquid concentrate or dried powder) containing many sea cucumber saponins from the location X in northern Japan is added to thereby manufacture a functional food or formulation containing a constant percentage of sea cucumber saponins.

This is explained more specifically using numerical values as shown in FIG. 7.

*Apostichopus japonicus* from location X in northern Japan were collected at a specific season when the sea cucumber saponin content was high, and treated under predetermined conditions (1.0° C./minute temperature gradient during temperature increase, 1.0° C./3 minutes temperature gradient during temperature decrease), and the sea cucumber saponin contents of the sea cucumber raw material, treated sea cucumber meat portion and extracted extract were measured as shown in FIG. 7.

With the present invention, 15 kg of sea cucumber meat and 40 kg of sea cucumber extract can be separated and extracted from 55 kg of sea cucumber raw material, and the two can be mixed, dried, and pulverized to obtain 5 kg of sea cucumber powder.

In this case, assuming no loss from drying and pulverization, it is calculated that $(0.283 \times 15 + 0.062 \times 40)/5 = 1.34$ mg/g of powder containing sea cucumber saponins (sea cucumber powder obtained by combining powders of sea cucumber meat portion and sea cucumber extract) can be obtained.

In terms of actual measurements, we could confirm that $1.25 \pm 0.037$ mg/g of sea cucumber powder was obtained, which is a yield of at least 93% relative to the calculated value of 1.34 mg/g.

With the present invention, at least 90% of sea cucumber saponins were retained even after the processes of drying and pulverization, indicating that the yield is high even though the sea cucumber is separated into a meat portion and a sea cucumber extract, and the saponin content can be adjusted even using sea cucumber raw materials from various production regions with differing sea cucumber saponin contents.

Supposing that a sea cucumber material or sea cucumber extract material with a sea cucumber saponin content of 0.7 mg/g is required as a functional food for treating *Candida* infection, if a sea cucumber material or sea cucumber extract material separated and extracted from a sea cucumber raw material collected from location Y in eastern Japan (or a sea cucumber powder obtained by mixing powders of the two) has a sea cucumber saponin content of about 0.2 mg/g for example, it cannot be used as is.

However, since a sea cucumber material or sea cucumber extract material separated and extracted from a sea cucumber raw material collected from location X in northern Japan (or a sea cucumber powder obtained by mixing powders of the two) has a sea cucumber saponin content of about 1.3 mg/g, a sea cucumber material or sea cucumber extract material (or a sea cucumber powder obtained by mixing powders of the two) with a level of $(0.2+1.3)/2=0.75$ mg/g in excess of the standard value can be obtained by mixing the two in equal proportions in the present invention.

Furthermore, if the weight of a powder obtained by freeze drying 40 kg of sea cucumber extract separated and extracted from a sea cucumber raw material from location X in northern Japan is 1 kg, a sea cucumber extract can be obtained with a content of $(0.062 \times 40)/1 = 2.48$ mg/g.

Thus, even if a sea cucumber extract material separated and extracted from a sea cucumber raw material from location Z in western japan has a low content of 0.1 mg/g or the like, the two can be combined to obtain a sea cucumber extract with a content of for example $(2.48 \times 0.25 + 0.1 \times 075) =$ about 0.7 mg/g that matches the standard level, so this sea cucumber extract materials from western Japan can be used without waste.

FIG. 7 shows the contents of sea cucumber saponins in the sea cucumber meat portion and sea cucumber extract after separation and extraction with predetermined temperature gradients, but this is only one example, and the separation and extraction ratios of the sea cucumber meat portion and sea cucumber extract can be altered at will as discussed below by changing the temperature gradient conditions.

Thus, with the present invention it is possible to separate a sea cucumber meat portion and sea cucumber extract from a sea cucumber raw material, and to appropriately adjust the proportions thereof, so that for example the sea cucumber meat portion can also be dried in its original shape rather than being pulverized, and provided as high-quality dried sea cucumber, while the sea cucumber extract containing sea cucumber saponins can be stored separately as a sea cucumber material (liquid concentrate or dried powder).

This can then be mixed with a sea cucumber material manufactured using sea cucumbers with a lower content of sea cucumber saponins as the raw material, and used as a foodstuff or formulation with a constant sea cucumber saponin content.

6. Other Examples for Maintaining Constant Content

When *Apostichopus japonicus* from location X in northern Japan were collected at a specific season (different from that of FIG. 7) when the sea cucumber saponin content was high as in FIG. 7, and treated under specific conditions (1.0° C./minute temperature gradient during temperature increase, 1.0° C./5 minutes temperature gradient during temperature decrease), the sea cucumber saponin contents of the sea cucumber raw material, treated sea cucumber meat portion and extracted extract were measured as shown in FIG. 8.

In this experimental example, because extraction was performed with the temperature reduced gently at a temperature gradient of 1.0° C./5 minutes during temperature decrease, the extracted amount of sea cucumber saponins was greater relative to the sea cucumber meat portion, so that 10 kg of sea cucumber meat portion and 45 kg of sea cucumber extract were obtained from 55 kg of sea cucumber raw material.

In this case, assuming no loss from drying and pulverization, it is calculated that $(0.44 \times 10 + 0.09 \times 45)/5 = 1.69$ mg/g of powder containing sea cucumber saponins can be obtained.

In terms of actual measurements, we confirmed that $1.58 \pm 0.039$ mg/g of sea cucumber powder was obtained, which is a yield of at least 94% relative to the calculated value of 1.69 mg/g.

7. Summary

As discussed above, it has been shown that with the present invention it is possible to adjust the extracted amounts of a sea cucumber meat portion and sea cucumber extract, and 90% or more of sea cucumber saponins are retained even when the extracted amount of sea cucumber extract is increased, so the yield is high even though the sea cucumber is separated into a meat portion and a sea cucumber extract, while the saponin content can be adjusted even when using sea cucumber raw materials from various production regions where the sea cucumber saponin contents are different.

Thus, because for example a powder containing the sea cucumber meat can have a residual odor that may be an issue if it is mixed with jelly or the like to make a functional food that is ingested in that form as a product, and also because the sea cucumber meat portion has a high product value by itself when the sea cucumber is spiny, the sea cucumber meat portion can also be dried as is and provided as dried sea cucumber for cooking.

Because the sea cucumber extract has little odor because it does not contain meat, moreover, it can be mixed with jelly or the like to provide a functional food that is effective for *Candida* infection treatment.

In this case, sea cucumbers can be collected with different sea cucumber saponin contents from different production regions, and used to manufacture a sea cucumber extract material (liquid concentrate, powder or the like) containing a constant percentage of sea cucumber saponins, which is then added to foodstuffs and the like to continuously provide products with a stable content ratio.

With the present invention, because a sea cucumber extract containing sea cucumber saponins can be separated from a sea cucumber meat portion and extracted from sea cucumbers simply by heat treatment mainly by adjusting the temperature gradients during temperature increase and temperature decrease and the like without chemical treatment with ethanol, enzymes or the like, it is possible to provide a saponin-adjusted material that is safe as a foodstuff.

INDUSTRIAL APPLICABILITY

Mainly saponins and the like including the holotoxin group including holotoxin A, holotoxin B, holotoxin A1 and holotoxin B1 out of the sea cucumber saponins can be extracted and mixed with jelly or the like to develop foodstuffs and the like having sea cucumber saponin activity, such as a jelly having a *Candida* suppressing function.

Alternatively, mainly frondoside A can be extracted out of the sea cucumber saponins, and provided as a powder or other formulation to develop foodstuffs and the like that suppress cancer cells.

REFERENCE SIGNS LIST

10 Extraction system of invention
20 Legs
30 Extract extraction part
40 Sea cucumber support part
50 Heating part (temperature adjustment part A)
60 Hot water
70 Steam
80 Temperature measurement part
90 Release valve adjustment part (temperature adjustment part B)
100 Sea cucumber (sea cucumber meat portion after extraction)
110 Extracted sea cucumber extract

The invention claimed is:

1. A method for extracting a sea cucumber extract containing a sea cucumber saponin from sea cucumbers by heat treatment, the method comprising:
   a step of providing sea cucumbers as a raw material having a body tissue containing a collagen fiber;
   a step of heating the sea cucumbers, before the collagen fiber dissolves, to an initial heating temperature;
   a temperature increase step in which a temperature of the sea cucumbers is increased from the initial heating temperature to at least a target heating temperature with a first temperature gradient being positive in a range of 0.7° C./minute to 1.5° C./minute, such that the collagen fiber in the sea cucumbers is denatured;
   a step of determining whether the initial heating temperature of the sea cucumbers has been increased to at least the target heating temperature;
   a temperature decrease step in which once the at least target temperature has been reached, the temperature of the sea cucumbers is decreased with a second temperature gradient being negative in a range of 1.0° C./2 minutes to 1.0° C./5 minutes such that a protein of the sea cucumbers is consolidated as a sea cucumber meat portion, and
   a step of determining whether the temperature of the sea cucumbers has been decreased during the temperature decrease step to at most a decrease target temperature, and
   the sea cucumber extract containing the sea cucumber saponin is separated from the sea cucumber meat portion and extracted from the sea cucumbers without any chemical treatment.

2. The method for extracting a sea cucumber extract according to claim 1, wherein the first temperature gradient is 1.0° C./minute and the second temperature gradient is 1.0° C./3 minute.

* * * * *